United States Patent [19]

Kuehl et al.

[11] Patent Number: 4,945,055
[45] Date of Patent: Jul. 31, 1990

[54] HUMAN CHORIONIC GONADOTROPIN RELEASING FACTOR

[75] Inventors: Thomas J. Kuehl; M. J. K. Harper; Gabriel S. Khodr; Theresa M. Siler-Khodr, all of San Antonio, Tex.

[73] Assignee: Board of Regents, University of Texas System, Austin, Tex.

[21] Appl. No.: 863,310

[22] Filed: May 15, 1986

[51] Int. Cl.$^5$ .............................................. C12N 9/64
[52] U.S. Cl. .................................. 435/226; 435/219; 435/267; 435/268; 435/269; 435/272
[58] Field of Search ............... 435/226, 219, 267, 268, 435/269, 272

[56] References Cited

U.S. PATENT DOCUMENTS 4,338,305  7/1982  Corbin .................................. 424/177

OTHER PUBLICATIONS

Seeburg et al., Nature, 311:666 (1984).
Lee et al., Acta Endocrinol., 96:394 (1981).
Tan et al., Biochem. Biophys. Res. Commun., 109:1061 (1982).
Siler-Khodr et al., Life Sci., 32:2742 (1983).
Siler-Khodr et al., Fertil. Steril., 41:448 (1984).
Gibbons et al., Am. J. Obstet. Gynecol., 121:127 (1975).
Siler-Khodr and Khodr, Am. J. Obstet. Gynecol., 130:216 (1978).
Siler-Khodr and Khodr, Fertil. Steril., 32:294 (1979).
Siler-Khodr et al., Am. J. Obstet. Gynecol., 150:376 (1984).
Khodr and Siler-Khodr, Fertil. Steril., 2:523 (1978).
Seppala et al., Clinical Endocrinol., 12:441 (1980).
Miyake et al., Obstet. Gynecol., 60:444 (1982).
Khodr and Siler-Khodr, Fertil. Steril., 30:301 (1978).
Siler-Khodr and Khodr, Biol. Reprod., 25:353 (1981).
Khodr and Siler-Khodr, Science, 207:315 (1980).
Siler-Khodr and Khodr, Fetal Endocrinology, Novy, Resko, Ed., Academic Press, New York, p. 183 (1981).
Siler-Khodr and Khodr, in Role of Peptides and Proteins in Control of Reproduction, Dhindsa McCann, Ed. Elsevier, North Holland, New York, p. 347 (1982).
Siler-Khodr, Clinics in Perinatol., 10:553 (1983)
Siler-Khodr, Sem. in Reproduct. Endocrinol., 1:321 (1983).
Siler-Khodr and Khodr, Endocrinology, 56:274 (Abstract #776) (1983).
Siler-Khodr et al., Scientific Program and Abstracts of the 31st Annual Meeting of the Society for Gynologic Investigation, San Francisco, California, Abstract No. 316:190 (1984).
Siler-Khodr et al., the 32nd Annual Meeting of the Society for Gynocologic Investigation, Phoenix, Arizona (1985).
Poisner et al., Federation Proceedings Abstract No. 1003, p. 326 (1986).
Gautron et al., Molec. Cell. Endocr., 24:1 (1981).
Seppala et al., Life Sciences, 25:1489 (1979).
Seppala et al., Life Sciences, 27:395 (1980).
Seppala and Wahlstrom, Int. J. Cancer, 26:267 (1980).
Eidne et al., Science, 229:989 (1985).
Dutlow and Miller, Biochem. Biophys. Res. Commun., 101:486 (1981).
Bhasin et al., Endocrinol., 112:1144 (1983).
Sokol et al., Biol. of Reprod., :370.

*Primary Examiner*—Robert A. Wax
*Attorney, Agent, or Firm*—Arnold, White & Durkee

[57] ABSTRACT

A substantially purified human chorionic gonadotropin releasing factor (hCG-RF) which is a glycoprotein with a molecular weight between about 50,000 and about 70,000. This hCG-RF is capable of stimulating release of human chorionic gonadotropin as well as prostaglandins, particularly from human term placental cultures. This hCG-RF is capable of degrading GnRH and is isolatable from human placenta, preferably term placenta. Such hCG-RF may be used to affect a state of pregnancy, particularly mammalian pregnancy. This effect upon pregnancy may comprise the induction of a normal labor.

12 Claims, 5 Drawing Sheets

HUMAN CHORIONIC GONADOTROPIN RELEASING FACTOR

The U.S. government may have rights concerning the present invention because relevant developmental work was supported by NIH grant No. HD 14852.

BACKGROUND OF THE INVENTION

The present invention is related to a newly discovered human chorionic gonadotropin releasing factor (hCG-RF) and its uses such as affecting states of pregnancy.

Gonadotropin releasing hormone-like material has been identified in various biological fluids or tissues such as hypothalami, semen, testes, placenta, pancreas or mammary. carcinoma, for example. It is generally believed that gonadotropin releasing hormone (GnRH) is identical or similar to luteinizing hormone releasing factor (LRF) and is a small peptide. This small peptide is generally agreed to be a decapeptide with the amino acid sequence: pyro-glu-his-trp-ser-tyr-gly-leu-arg-pro-gly-$NH_2$. Gn-RH-like material appears to be synthesized by placenta and numerous other tissues as well as to have receptor sites in diverse organs. The present invention describes a human chorionic gonadotropin releasing factor (hCG-RF) which has never before been identified and is completely unique in many ways from GnRH. Antibodies directed toward GnRH have indicated the presence of GnRH-like material at numerous other biological sites. A 92 amino acid peptide has been reported which contains the decapeptide GnRH (Seeburg et al., Nature (1984) V. 311, p. 666), but the human chorionic gonadotropin releasing factor (hCG-RF) described herein differs from it.

Earlier studies have demonstrated that an immunologically and biologically active GnRH was synthesized and released from human placental extracts. This GnRH eluted from CM-cellulose in the same area as synthetic GnRH. In addition, Lee at al. (Acta Endocrinol. (1981) V 96 p 394) reported a apparent GnRH immuno-activity from acid extracts of placentas that eluted on HPLC in the area of GnRH. These findings led to the hypothesis that placental apparent GnRH immuno-activity and synthetic GnRH were chemically similar. Additionally Tan et al. (Biochem Biophys. Res. Commun. (1982) V 109 p 1061) reported that the GnRH decapeptide sequence was present in the acid extracts of placenta. More recently, Seeburg et al (Nature (1984) V 311 p 666), using cDNA expression, have deciphered an mRNA coding for 92 amino acids in which the GnRH sequence is contained.

Certainly, the presence of the decapeptide GnRH in the placenta has been firmly supported. The role of GnRH in placental endocrinology has not been answered by the above cited studies. It has been demonstrated that synthetic GnRH can affect placental hormonogenesis, yet high concentrations are needed. An antagonist of GnRH has been shown to inhibit placental hormonogenesis both in vitro (Siler-Khodr et al, Life Sci. (1983) V. 32, p. 2742 and Siler-Khodr et al., Fertil-Steril (1984) V 41 p 448) and in vivo. Other studies have demonstrated that a placental receptor recognizes synthetic GnRH; however, the dissociation constant of the placental receptor for synthetic GnRH was found to be only $10^{-7}M$ and a potent antagonist of GnRH on the pituitary had no greater affinity for this placental receptor than did GnRH. Thus, it appeared that the placental receptor recognizing synthetic GnRH differed from the pituitary receptor. The inventors have also noted that, although there was newly synthesized apparent GnRH immuno-activity recovered in the GnRH area following CM cellulose chromatography, it accounted for <1% of the apparent GnRH immuno-activity. In addition as reported herein, it was observed that apparent GnRH immuno-activity of the placenta was extracted with a very low yield with methods typically utilized for extraction of hypothalamic GnRH, i.e. acid or methanol. These findings led the inventors to consider the possibility of there being more than one substance effecting this activity in the human placenta.

SUMMARY OF THE INVENTION

The present invention broadly comprises a substantially purified human chorionic gonadotropin-releasing factor (hCG-RF) which is a glycoprotein with a molecular weight between about 50,000 and about 70,000. This hCG-RF is capable of stimulating release of human chorionic gonadotropin as well as prostaglandins, from human placental cultures. This hCG-RF is capable of degrading GnRH such that it is no longer immunologically or biologically active. This hCG-RF is isolatable from human placenta. Such hCG-RF may be used to affect a state of pregnancy, particularly mammalian pregnancy. Such effects upon a state of pregnancy may comprise the induction of labor.

from human term placental cultures incubated in Medium 199, Medium 199 with 8.33 uM GnRH, Medium 199 with hCG-RF (50.0 nM, 100 nM and 200 nM). The hCG-RF-containing media was spiked on days 5 and 6 with additional 14.6, 29.2, 43.7 nM hCG-RF respectively.

Figure 7:
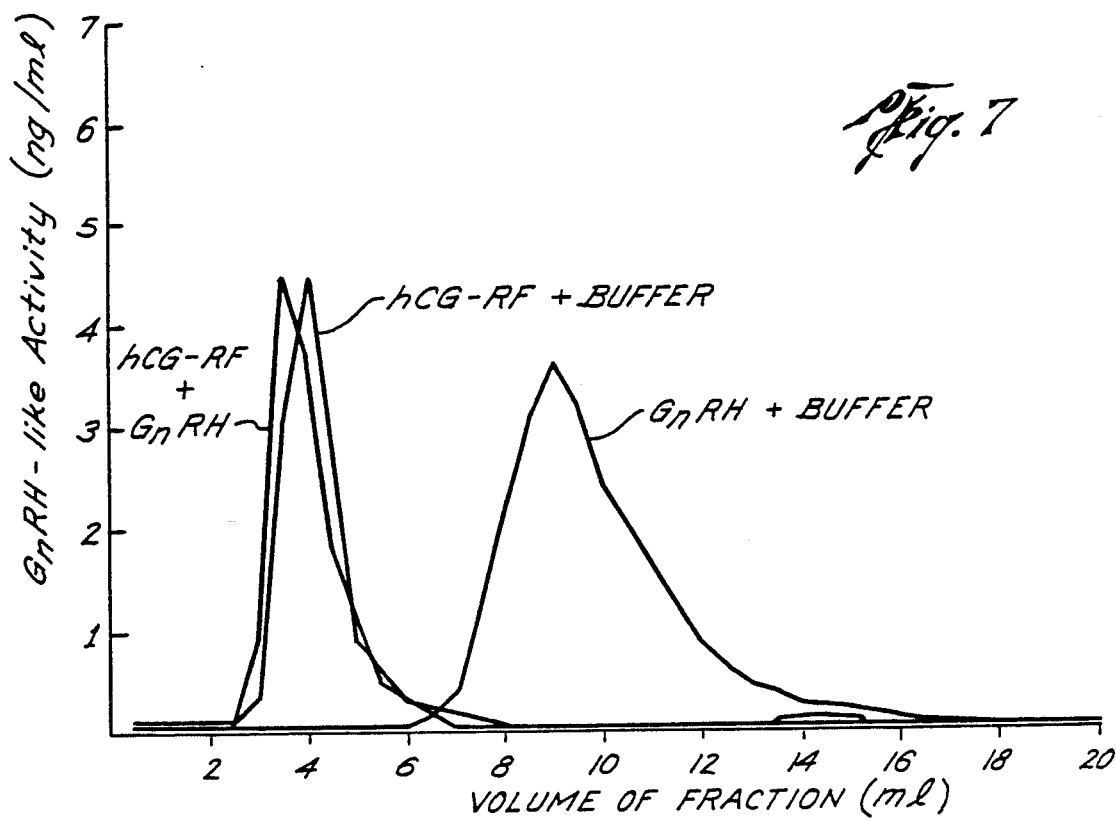

FIG. 7 shows the elution patterns for Sephadex G-150 of immunoactive GnRH treated with hCG-RF or with buffer.

Figure 8:
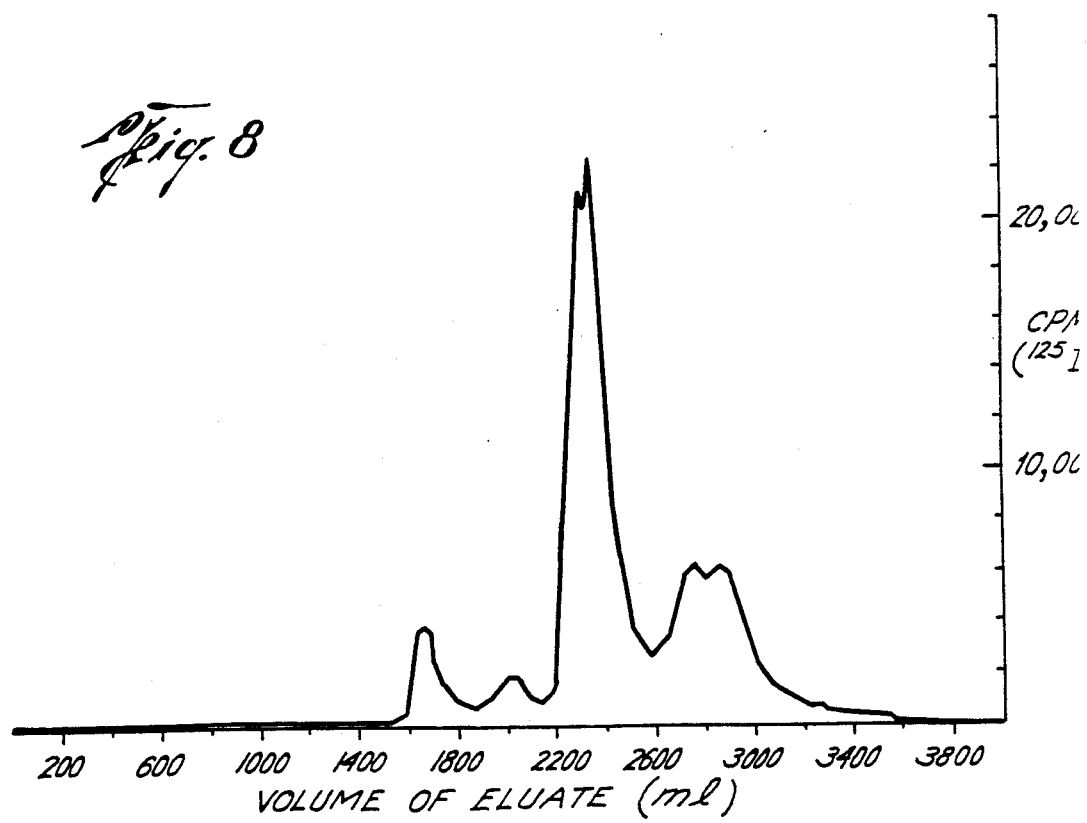

FIG. 8 shows a radioisotopic elution pattern from Sephadex G-25 of 125I-GnRH treated with an hCG-RF preparation.

DESCRIPTION OF PREFERRED EMBODIMENTS

A glycoprotein that stimulates the release of alphahCG, hCG, prostaqlandin E (PGE) and 13,14-dihydro-15-keto prostaglandin F (MPF) from placental explart cultures and that degrades GnRH has been isolated from human term placentas and a 4000-fold purification effected. This endogenous human chorionic gonadotropin releasing factor (hCG-RF) has an apparent mol. wt. of between about 50,000 daltons and about 70,000 daltons, most likely about 60,000 daltons, as estimated by SDS-PAGE and HPLC analysis. This hCG-RF contains carbohydrate as determined by Schiff's periodate staining of the SDS-PAGE protein bands. As little as 25 nM purified hCG-RF stimulated placental alpha-hCG, hCG, PGE and MPF release with a potency much greater than that of synthetic GnRH, i.e. 100, 230 and 600 times, respectively. A large part of the endogenous apparent GnRH immuno-activity in the placenta is present as an about 60,000 mol wt glycoprotein, which degrades GnRH and has potent biologic activity in stimulating hCG and prostaglandin release. During the development of this invention it was noted that 99% of the endogenous apparent GnRH immuno-activity in the human placenta was due to a glycoprotein with an apparent mol wt of about 60,000 (hCG-RF). This hCG-RF had a much greater bioactivity on placental hormone release than did the decapeptide, GnRH.

During the course of characterizing hCG-RF, it was discovered that this substance may be doing more than immunogenically competing with GnRH. An apparent peptidase activity was found to reside in hCG-RF fractions. This peptidase activity appeared to degrade GnRH decapeptide to smaller fragments and thus diminish its immunoactivity. Thus the term "apparent immunoactivity" as used herein may refer to immunological competition and/or an alteration of GnRH. This alteration may be due to a hydrolytic degration or another type of activity.

The following Examples are presented to illustrate preferred embodiments of the present invention and to be enabling descriptions. These Examples are not meant to limit the claims of this patent unless otherwise specifically so stated in these claims. Examples 1–8 illustrate materials and methods applicable to the present description. Examples 9–16 illustrate results accomplished.

EXAMPLE 1

Placental Extractions

Human placentas were obtained following normal term deliveries from patients admitted to the Obstetrics Unit of the Medical Center Hospital (San Antonio, Tex.). Placental tissue was dissected free of membranes and vessels and the lyophilized. The freeze-dried tissue was pulverized and extracted. The extraction efficiency was compared using different procedures. Samples of pulverized, freeze-dried placental tissue (40 g each) were each suspended in 500 ml of one of the following solutions: (1) 0.1M $NaHCO_3$, with 50 mM para-amino benzamidine (pab) pH 9.0; (2) 0.05M Na pH 7.5; (3) 0.01M Tris, pH 7.6; (4) 0.01M Hepes, pH 7.0; (5) 0.1 M $CH_3COOH$; (6) 90% methanol; (7) 2M $CH_3COOH$ and boiled for 30 min; (8) 10% trichloracetic acid; or (9) 100% acetone. The suspension was stirred for 10 min and then the supernatant was collected following filtration through a Buchner funnel. The methanol and acetone extracts were vacuum dried at room temperature and resuspended in distilled $H_2O$. The total apparent GnRH immuno-activity recovered with each extraction method was cuantitated in the GnRH radioimmunoassay (RIA) obtained from using aliquonts of $\leq 10\mu l$ (microliter) of the resultant extracts.

EXAMPLE 2

Initial Characterization Of nCG-RF Activity

Freeze-dried term placentas were extracted with 10 mM Tris, dithiothreitol and 0.0004% pepstatin, pH 7.0 (Tris-DTT-pepstatin buffer, 300 ml per placenta). Other buffers effective at about this pH and certain other protease inhibitors or sulfhydryl compounds should give equally satisfactory results. The compounds Sephadex, Tris and DEAE are lab reagents employed by those skilled in the art of molecular characterization of proteins. Sephadex is an ion exchange substance characterized by bead size and used in the gel filtration for fractioning molecules of large molecular weight, such as proteins. Tris is chemically defined as tris(hydroxymethyl) amino-methane. As used by those of skill in the art and as used in the Specification, the abbreviation DEAE refers to diethylamino ethyl. Following centrifugation at 4000× g for 30 min. at 4° C., various studies were performed and are described as follows.

(1) Differential Centrifugation.

The solubility of the apparent GnRH immuno-activity in the placental extract was monitored by RIA before and after centrifugation. The supernatant and precipitate (resuspended in distilled $H_2O$) from the placental cell extracts following rentrifugation at 4,000 — g were obtained. The supernatant was centrifuged at 10,000 — g and aliquants of the resulting supernatant and precipitate assessed for apparent GnRH immuno-activity. The 10,000 — g supernatant was then centrifuged at 40,000 — g and the apparent GnRH immuno-activity in the resultant supernatant and precipitate determined. Finally, the 40,000 — g supernatant was subjected to ultracentrifugation at 100,000 — g for 30 min and the apparent GnRH immuno-activitY in the resultant supernatant and precipitate determined.

(2) Precipitation of Apparent GnRH Immuno-Activity.

The effect of protein precipitation using either 70% ethanol, 70% methanol or 90% acetone on the apparent GnRH immuno-activity of the placental extract was also studied. Following solvent addition and centrifugation (3000 — g for 10 min), the apparent GnRH immuno-activity of the vacuum-dried supernatant was measured. Similar studies using synthetic GnRH were also performed.

(3) Ultrafiltration.

Diaflo ultrafiltration (Amicon Corp., Danvers, Mass.) of placental extracts containing apparent GnRH immuno-activity was performed using PM30, PM10, UM20, UM10, UM05 and UM02 membranes and the apparent GnRH content of the retentate and the filtrate measured by GnRH-RIA.

(4) Gel Filtration.

Sephadex gel chromatography (Sephadex G-200, G-150, G-100, G-75, G-25 [on 90×5 cm columns], equilibrated in Tris-DTT-pepstatin) was performed for placental extracts containing apparent GnRH immuno-activity and the elution of the apparent GnRH immuno-activity was determined with the GnRH-RIA. Molecular wt was estimated by comparison to bovine serum albumin (BSA) and synthetic GnRH.

(5) Incubations.

Attempts to displace, dissociate or denature this high-mol-wt apparent GnRH immuno-activity were done using $^{125}$I-labeled GnRH, guanidine, urea, Triton X-100, acid or boiling. Placental extracts (75 ml) were incubated with $^{125}$I-GnRH (5,000,000 cpm/ml final concentration) overnight at 4° C. Control incubations of both placental extracts and diluent (no labeled GnRH added) or $^{125}$I-GnRH and buffer (no placental extract added) were also done. Sephadex chromatography (G-150, 90×5 cm in Tris-DTT-pepstatin buffer) was performed on each incubate to determine possible displacement of the low mol wt $^{125}$I-GnRH to the area of the high mol we apparent GnRH immuno-activity. Eluates were monitored by both radioactive counts and immuno-activity.

Incubations of the placental extracts with either 3 or 6M guanidine, pH 7.5 for 0, 10, 20, 30, 40—, 60, 120, or 240 min at room temperature were performed. The resulting incubates were assayed for apparent GnRH immuno-activity. Buffer controls were included in each assay to determine if the assay binding was affected. Similar timed studies using 1 or 2M urea were also done. Placental extracts containing apparent GnRE immuno-active material were also incubated with 1% Triton X-100 for 3 h, at room temperature followed by chromatography of the incubate on Sephadex G-100. Similar studie's incubating synthetic GnRH rather than placental extracts with guanidine, urea or Triton X-100 were done for comparison. Molecular dissociation and/or digestion of the high mol wt apparent apparent GnRH immuno-activity were also attempted by incubating placental extracts with 0.1M CH$_3$COOH, 0.2M CH$_3$COOH, (30 min.), 2M CH$_3$COOH, or boiling in 2M CH$_3$COQH for 30 min. Incubates which contained apparent GnRH immuno-activity were then chromatographed on Sephadex G150, 75 or 25 at 4° C. to determine the apparent molecular size of the remaining apparent GnRH immuno-activity. Similar studies using synthetic GnRH rather than placental extracts were done for comparison.

EXAMPLE 3

Substantial - Purification of the High Molecular Weight Apparent GnRH Activity in Placenta, i.e. Human Chorionic Gonadotropin Releasing Factor (hCG-RF)

Extraction of an individual lyophilized, pulverized term placenta was done at room temperature, beginning with two acetone washes (1000 ml each). This initial step defatted the tissue without extracting the apparent GnRH immuno-activity, and was followed by extraction of the apparent GnRH immuno-activity from the acetone precipitate with 300 ml of 0.01M Tris-DTT-pepstatin buffer. Pepstatin was also included in the buffer to preserve the apparent GnRH immuno-activity during storage and purification, and DTT to prevent aggregation of the material with apparent GnRH immuno-activity. The placental suspension was centrifuged in a IEC PR-6000 centrifuge at 4° C. at 3000— g for 30 min and the supernatant (total volume, 160 ml) was purified by chromatography on Sephadex G-150 (5—90 cm, in Tris-DTT-pepstatin buffer) at 4° C. Approximately 80 ml of extract was applied to a column; thus, two columns were done for each placenta. The elution of apparent GnRH immuno-activity from these columns was determined using the two different GnRH-RIAs and the fractions containing the apparent GnRH immuno-activity (600 ml, Ke=0.27–0.40) were pooled and concentrated using a Diaflo hollow fiber filter (HIP30-20).

This partially purified concentrate (60 ml) of apparent GnRH immuno-activity was applied to a DEAE-Sepharose column (2.5×70 cm), equilibrated in 0.01M Tris, 0.001 M DTT, pH 7.4 (Tris-DTT). By this stage of the isolation, pepstatin was no longer needed to preserve the apparent GnRH immuno-activity. After application of the sample, the column was washed with the Tris-DTT buffer (350 ml), followed by Tris-DTT containing 0.1 M NaCl (1000 ml). The apparent GnRH immuno-activity was then eluted while washing with Tris-DTT containing 0.11 M NaCl (1600 ml). A final wash (400 ml) of Tris-DTT containing 1M NaCl was applied. The purified apparent GnRH immuno-activity which eluted with 0.11 M NaCl was physically, chemically and biologically distinct from GnRH as described below. Thus it was named human chorionic gonadotropin releasing factor (hCG-RF).

EXAMPLE 3A

Physical and Chemical Characterization and Assessemtn of Purity of hCG-RF

(1) Polyacrylamide Gel Electrophoretic Analysis (PAGE).

The hCG-RF activity. eluted following DEAE-Sepharose chromatography was studied by PAGE. PAGE was performed after pre-incubation of the purified hCG-RF for 30 min with 1% SDS. The sample was mixed 1:1 with 30% sucrose and layered on polyacrylamide gels of 7.2, 10, and 12.5% polyacrylamide content in a borate-tris buffer, pH 7.6, containing 0.1% SDS and 0.001M DTT, electrophoresis was performed at room temperature with the same buffer. Coomassie Brilliant Blue R-150 (0.1% in CH$_3$OH:H$_2$O:HOAc [5:5:1]) for 1 h was used to stain the protein. The gels were destained by washing with CH$_3$COOH:CH$_3$OH:-H$_2$O (10:5:85) 10 times, a single band was observed and its corresponding molecular weight estimated by comparison to standard proteins (phosphorylase B, BSA, ovalbumin, carbonic anhydrase, trypsin inhibitor and lysozyme) run concurrently on separate gels. The purified hCG-RF also migrated as one band after PAGE in the absence of SDS at pH 8.3.

(2) Carbohydrate Detection.

Figure 3:
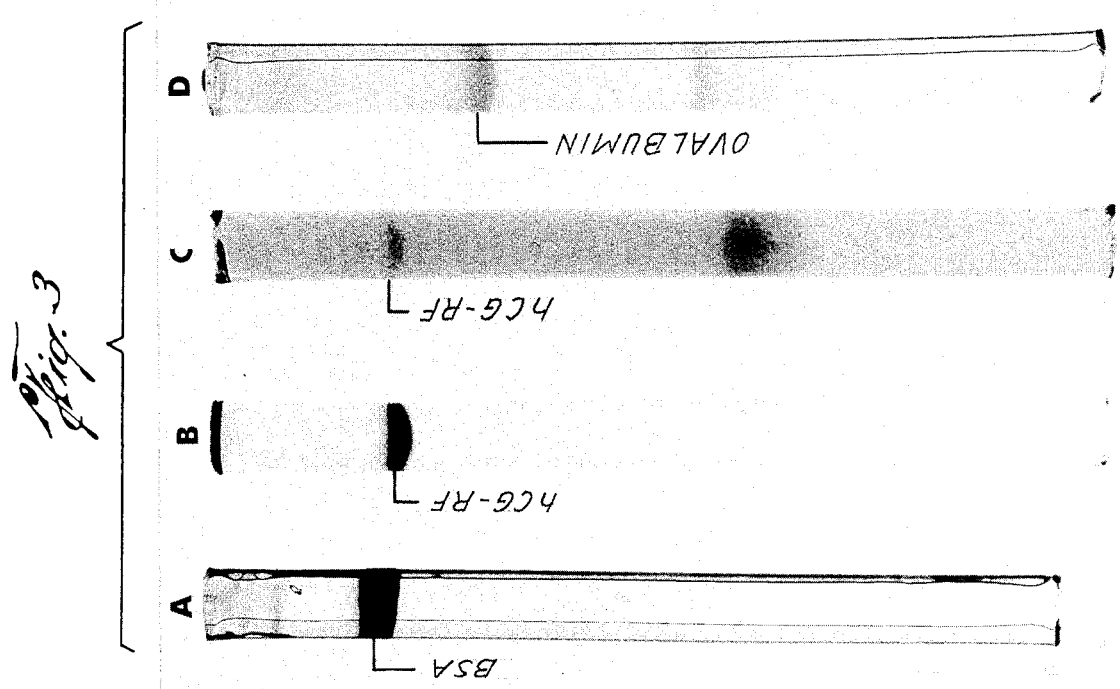
FIG. 3 describes PAGE gels for (a) BSA, (b) hCG-RF, (c) hCG-RF and (d) ovalbumin. Gels a and b were stained with Coomassie Brilliant Blue for protein and gels c and d with Schiff's periodate stain for sugars. The second band on the lower part of the c and d gels was due to the 15% sucrose added to the sample for ease of application.

Carbohydrate was detected using Schiff's Periodate staining. Highly purified hCG-RF, obtained following HPLC (fraction 14), was incubated with 1% SDS at room temperature for 30 min mixed 1:1 with 30% sucrose and applied to PAGE. Electrophoresis was done as described above in 0.1% SDS in buffer, pH 7.6. For both the hCG-RF and standard (as listed above), quadruplicate gels were stained with either 0.1% Coomassie Brilliant Blue (2 gels) or reacted with the Schiff's Periodate reagents (2 gels). Glycoproteins and sucrose were visualized in the Schiff's Periodate stained gels and all proteins stained with Coomassie Brilliant Blue. FIG. 3 shows PAGE gels with stained hCG-RF and protein standards (gels 9 and b, Coomossie Brilliant Blue protein stain; gels c and d Schiff's periodate carbohydrate stain).

(3) Molecular Wt and Purity Determined by HPLC.

Figure 4:
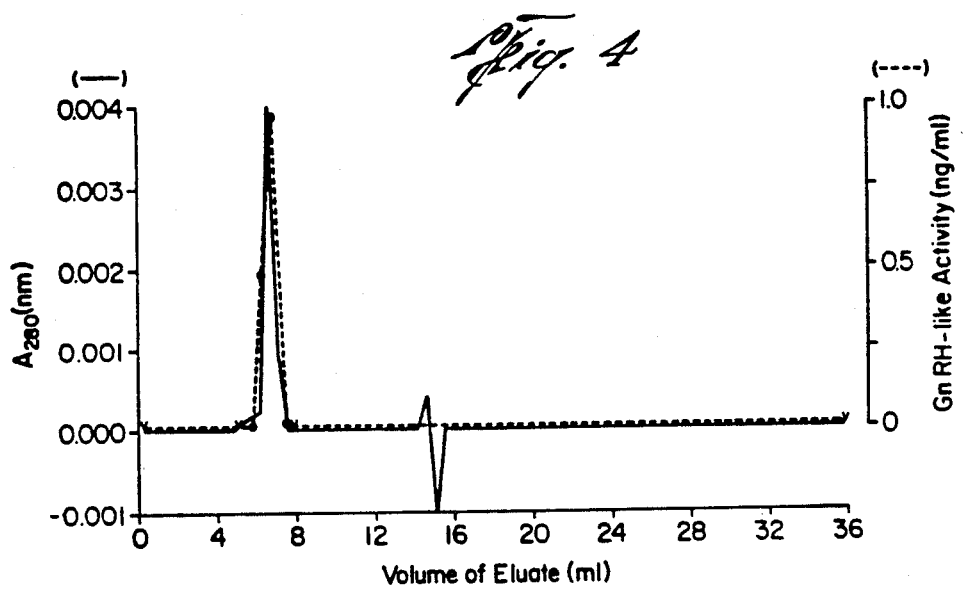
FIG. 4 describes the chromatogram (A280 nm) following HPLC of highly purified hCG-RF (25 ug) on a permeation column (BioRad TSK-250), in 0.01M Tris, 0.001M DTT (pH 7.2) with a flow rate of 1.0 ml per min. The second reading at 14–15 min was due to glycerol added to the sample prior to storage at −20° C. The hCG-RF (as determined from its apparent GnRH immuno-activity) eluted at 6.5 to 7.0 min as did the protein peak. Using the same solvent system, synthetic GnRH eluted at 22-25.5 min.

Highly purified hCG-RF fractions obtained following DEAE-Sepharose chromatography were studied by high pressure liquid chromatography (HPLC). Using a molecular sizing column of Biorad TSK-250 (Bio-Rad Laboratories, Richmond, CA) equilibrated in 0.01M Tris-HCl, 0.001M DTT, pH 7.2, the purified hCG-RF was eluted. Molecular wt was estimated by comparison to standards (thyroglobin, gamma globulin, ovalbumin, myoglobin, vitamin B-12) using the same buffer at a flow rate of 1.0 ml per minute. Absorbency was monitored at 280 nM. Apparent GnRH immuno-activity was determined by RIA in the fractions collected. Re-chromatography of the immuno-active hCG-RF fractions was done on the TSK-250 column to confirm its elution patterns. FIG. 4 shows the elution pattern of hCG-RF from the TSK-250 column.

(4) Trypsin Digestion.

Highly purified hCG-RF was incubated with two concentrations of trypsin (0.02 and 1 mg/ml) for 30 min at 37° C. The apparent GnRH immuno-activity in the resulting incubate and elution of apparent GnRH immuno-activity following HPLC chromatrography (as described above) was determined. The hCG-RF incubated with 1 mg/ml trypsin was further incubated at room temperature for 1 h and the apparent GnRH immuno-activity again determined following HPLC chromatography. The results of trypsinization are described in Example 10.

EXAMPLE 4

DETERMINATION OF hCG-RF BIOLOGICAL ACTIVITY (1) Activity on Placental Explants in Vitro.

The effect of purified hCG-RF on placental hormonogenesis was studied using explants of human term placentas. The culture system was a typical placental culture system for example as described by Siler-Khodr et al (Biol. Reprod. (1981) V 25 p 353). Quadruplicate cultures were done with: (1) Medium 199; (2) Medium 199 containing synthetic GnRH (8.33 uM); or (3) Medium 199 containing purified hCG-RF (50, 100 or 200 nM). Cultures were continued for 1 to 6 days, with media changed daily. On the fifth and sixth day of culture, to the media containing 50, 100, and 200 nM hCG-RF, an additional 14.6, 29.2, and 43.6 nM hCG -RF, respectively, was added. Two different normal human term placentas were studied. The concentrations of hCG, alpha-hCG, alpha-hCG and series E prostaglandins (PGE) and 13,14-dihydro-15-keto prostaglandin in the culture media were determined by radioimmunoassay (RIA). Data were converted to total hormonal release per wet wt of placental tissue cultured. The mean (±SEM) for each hormonal release from each set of quadruplicate samples was calculated.

(2) Activity on Pituitary LH and FSH Release in Vivo.

The effect of purified hCG-RF on pituitary LH and FSH release was studied in rats. Intact adult male rats were catheterized under ether anesthesia, the right external jugular vein was exposed and a polyethylene cannula (o.d.=0.038 in) inserted down to the level of the . right atrium. The rats were allowed to recover for at least 3 h before the studies were begun. Thus, these studies were performed in unanesthetized animals. Two basal blood samples were drawn 10 min apart. Purified 7 hCG-RF, 2.1 nM (n=5) or 0.001–0.004 nM GnRH (n=5) was injected as a single bolus controls (n=5) were injected with normal saline. Blood was drawn at 0, 10, 20, 30, 40, 50, 60, 75, 90 and 120 min. Plasma (EDTA) was collected and stored frozen at −20° C. until assayed for LH. The effect of purified hCG-RF on LH release from rat pituitary cell cultures was also studied. Doses of $10^{-6}$ to $10^{-9}$M were added to the culture medium and the release of LH in the following 4 hours was determined using the LH radioimmunoassay. The bioactivity of hCG-RF is described in Example 12.

EXAMPLE 4A

Alterations of GnRH by hCG-RF

The effect of purified hCG-RF on GnRH immunoreactivity was studied. HCG-RF (41 ug in 0.1 ml 0.01M TRIS-HCl, 0.001M DTT, 5% Glycerol, pH 7.2) and GnRH (40 ng in 0.1 ml of 0.5% BSA in PBS, pH 7.6) together with 0.1 ml buffer (0.01 M TRIS-HCl, 0.001M DTT, pH 7.2) and 0.015 ml marker dyes (15 mg Dextran Blue and 0.5 mg Bromophenol Blue, 150 mg sucrose and 1 mg KI per ml H$_2$O) were incubated 24 h at 4° C. Chromatography of 0.1 ml of the incubate on Sephadex G-150 (1×20 cm in 0.01M TRIS, 0.001M DTT) followed, collecting 1 ml fraction. Immunoreactive GnRH was determined by GnRH-RIA. GnRHimmunoreactivity and was completely lost. The elution patterns from this Sephadex G-150 is shown in FIG. 7. Addition of 175 mM para-amino-benzamidine, or 5000 unit bacitracin with the buffer totally reversed the loss of GnRH immunoreactivity effected by incubation with hCG-RF.

Partially purified hCG-RF (75 ml, 100 ug 0.01M TRIS, 0.001M DTT, 0.0004% Pepstatin, pH 6.8) was incubated with $^{125}$I-GnRH (10,000,000 cpm in 1 ml 1M NH$_4$oAc, pH 7.6) for 24 h at 4° C. The incubate was applied to a Sephadex G-25 column (2.5×90 cm, in 0.01M TRIS-HCl, 0.001M DTT, pH 7.2). Elution of $^{125}$I was determined by gamma scintillation counting and four peaks having a mol wt smaller than GnRH as well as one corresponding to GnRH were found. The elution patterns from this Sephadex G-25 are shown in FIG. 8.

EXAMPLE 5

Rasioimmunoassays (1) Peptide Hormones.

Radioimmunoassays were carried out by radioimmunoassay (RIA) described previously by Siler-Khodr et al (Biol. Reprod. (1981) V 25 p 353). All determinations for the culture media from a given placenta were performed in the same assay. In each assay, each culture medium was tested for interference with the maximum binding or non-specific effects: None was found.

(a) GnRH.

Two different antisera were used to detect and quantitate the cross-reacting apparent GnRH immuno-activity of the human placenta. Synthetic GnRH was radio-iodinated by the method of Hunter et al (Nature (1962) V 194 p 495) and desalted on a CM-cellulose. column. $^{125}$I-GnRH (20 pg/100 ul) was added to each assay tube. One GnRH antibody used (UZ-2; Miles Laboratory, Elkhart, Ind.) was made to a GnRH-bovine serum albumin (BSA) conjugate and used at a final dilution on 1/30,000. Standard was synthetic GnRH. There was a 20% cross-reaction with the C-terminal nonapeptide. Other fragments and the free acid had less than a 2.5% cross-reactivity. Diluent used in these assays was 0.5% BSA. Thus, all anti-BSA population of this antiserum was fully saturated and the cross-reactivity with crystalline BSA (Sigma No. A-7638, St. Louis, Mo.) was <0.0000008%. Human serum albumin (Sigma A-9511) also had cross-reactivity of <0.0000003%. Apparent GnRH immuno-activity reported herein was determined using this assay unless otherwise stated. No significant cross-reaction (<0.001%) with hCG, beta-hCG, alpha-HCG or hCS was observed. Standard was synthetic GnRH. The assay sensitivity was 8 pg/tube and the assay coefficients of variation were 3% and 7%, respectively, at 70% of the maximum binding.

The other GnRH antibody used was a monoclonal antibody to GnRH. This antiserum was used at a final titre of 1/1,000,000 and was highly specific for GnRH. Standard was synthetic GnRH. The antiserum was directed to the Nterminal pentapeptide sequence of GnRH and crossreactivity with BSA was <0.000008% and HSA, <0.000003% in this assay. Assay sensitivity was 4 pg/tube and the within and between coefficients of variation were 5% and 9%, respectively, at 70% of the maximum binding.

(b) Alpha-hCG.

Quantitation of alpha-hCG was done using a specific antiserum for this subunit (SA6 provided by the NIAMDD, National Institutes of Health, Bethesda, Md.), at a final dilution of 1,100,000. Purified alpha-hCG was radio-iodinated to a specific activity of 500–600 uCi/ug, and 0.100 μg added to every tube. The standard was purified alpha-hCG. Incubation of antibody, label, and standard or sample was for 16 h at 4° C. Separation of bound and free hormone, counting, and calculations were standard as described previously by Siler-Khodr et al (Biol. Reprod. (1981) V 25 p 353). The assay sensitivity was 0.04 ng/tube and the within and between assay coefficients of variation were 9.2% and 12.0%, respectively, at 70% of the maximum binding. A nanogram of purified alpha-hCG (NIH) was equivalent to 70 mIU of the Second International Standard for hCG. Intact hCG was indistinguishable from alpha-hCG in this assay, and cross-reactivity with the intact pure hCG in this system was 18% (ng:ng). Cross-reaction with beta-hCG was <0.4% and GnRH, <0.001% (ng:ng).

(c) hCG.

Measurement of hCG was done using a specific antiserum to the beta subunit of hCG at a final dilution of 1/1,000,000. Purified intact hCG (CR-119) was radio-iodinated to a specific activity of 200–300 uCi/ug and 0.100 ng was added to each tube. Antibody, label, and standard or sample were incubated for 16 h at 4° C. Separation of bound hormone, counting and calculations were as described by Siler-Khodr et al (1981). Assay sensitivity was 0.100 ng/tube, and the within and between assay coefficients of variation were 10.0% and 12.3%, respectively, at 70% of the maximum binding. One ng of hCG (CR 119) was equivalent to 0.5 ng purified beta-hCG and 3.5 mIU hCG (Second International Standard for hCG). Cross-reactivity of alpha-hCG in this system was 0.008%. No significant cross-reactivity with GnRH (<0.001%) was observed. Thus, this assay was highly specific for intact hCG or its beta subunit.

(d) Rat LH.

Measurement of rat LH was done using an antiserum to ovine LH at a final dilution of 1/75,000.

Purified ovine LH (#LER 1374A provided by NIAMDD) was radioiodinated using the method of Hunter et al (1962) to a specific activity of 300–400 Ci/ug and 0.100 ng was added to each tube. Standard was LH (RP-1). The standard or sample and antiserum were preincubated overnight at 4° C. Label was then added and the incubation continued for another day at 4° C. before adding the anti-rabbit gamma globulin. Assay sensitivity was 0.4 ng/tube and the coefficient of variation within and between assays was 2.1% and 6.8% of the maximum binding, respectively.

(2) Prostaglandins.

Prostaglandin E and 13,14-dihydro-keto prostaglandin F were measured in direct aliquants of culture media (<100 ul) using specific antisera. Similar aliquants of culture media incubated without placental tissue were included in each assay as buffer controls. No effect on the maximum binding or non-specific binding was found. All samples from a given placental culture set were measured in the same assay. To each tube, 100 ul of specific antiserum in phosphate buffered saline (PBS) (nonspecific binding tubes contain only PBS) was added. [$^3$H]-Prostaglandin (100 ul) at a concentration of 500 pg/ml PBS containing 1% bovine gamma globulin was added to each tube. Final incubation volume was adjusted to 0.5 ml with PBS. Incubation was overnight at 4° C. and the antibody-bound ligand was then precipitated by mixing with 2.0 ml of 40.5% polyethylene glycol, with 0.001M $CaCl_2$. Following centrifugation at 1500 — g for 30 min, the supernatant was decanted and the precipitate resuspended with 0.2 ml 0.1 N NaOH. Scintillation fluid (3 ml of the following mixture: 6 g PPO, 0.3 g POPOP, 0.9 liter toluene, 0.1 liter Biosolv BBS-3, Beckmann, Inc.) was added to each tube and shaken for 10 min. Each tube was counted to 2% efficiency, the B/Bo ratio was computed after correction for nonspecific binding and the prostaglandin concentration was calculated against the logit-log fit of the appropriate standard.

(A) Prostaglandin E.

A specific antiserum for prostaglandin E was obtained from Seragen Inc. (Boston, Mass.) and used at a final dilution of 1/21,000. Label was [5,6,8,11,12,14,15 (n)—$^3$H ]prostaglandin $E_2$ purchased from Amersham Corp. (Arlington Heights, Ill.). Assay sensitivity was 8 pg/tube and the intra- and interassay coefficients of variation were 11% and 17%, respectively.

(B) 13,14-Dihydro-15-keto prostaglandin F.

A specific antiserum to 13,14-dihydro-15-keto PGF, was used at a final dilution of 1/125,000. Label was 13,14-dihydro-15-keto [5,6,8,9,11,12,14-(n)-$^3$H]prostaglandin $F_2$ alpha purchased from Amersham Corp. (Arlington Heights, Ill.). Assay sensitivity was 7 pg/tube and the intra- and interassay coefficients of variation were 10% and 15%, respectively.

EXAMPLE 6

Protein Measurement and Statistical Analysis

Protein concentration was determined by the Lowry method as described by Bradford (Anal. Biochem. (1976) V 72 p 248) or by absorbance at 280 nm using crystalline bovine serum albumin as standard. For release of each hormone from a given placenta the variatior of the response with hCG-RF was compared to that of the controls or that of GnRH-stimulated cultures using two-way analysis of variance. Dose-response analysis was done using linear regression analysis.

EXAMPLE 7

Placental Extraction

The effectiveness of various buffers for extracting the apparent GnRH immuno-activity from placental tissue is compared in Table 1. Relatively neutral buffers, i.e. 0.01M Tris (pH 7.6), 0.01M Hepes (pH 7.0), 0.05M Na$_2$HPO$_4$ (pH 7.5), each yielded approximately 5 ug apparent GnRH immuno-activity/placenta. The more classical procedures of acid or methanol, as used fcr hypothalamic GnRH, resulted in a very low yield of apparent GnRH immuno-activity from the human placenta (0.2%–4.0%). The extremely poor recovery in the acetone extraction (0.02%) followed by extraction of the apparent GnRH immuno-activity from the precipitate using any of the neutral buffers demonstrated that most of the apparent GnRH immuno-activity of the placenta was acetone precipitable. Synthetic GnRH was not precipitated by acetcne.

TABLE 1

EXTRACTION OF APPARENT GnRH IMMUNO-ACTIVITY FROM HUMAN TERM PLACENTAS

| Extraction buffer | Apparent GnRH activity (μg/placenta) | Yield (%) |
|---|---|---|
| 0.1 M NaHCO$_3$, pH 9.0, 50 mM pab at RT | 5 | 100 |
| 0.05 M Na$_2$PO$_4$, pH 7.6, 0.0004% pepstatin at RT | 5 | 100 |
| 0.01 M Tris-HCl, pH 7.6, at RT | 5 | 100 |
| 0.01 M Hepes, pH 7.0, at RT | 5 | 100 |
| 0.1 M CH$_3$COOH, 0.0004% pepstain at RT | 0.3 | 6.0 |
| 2.0 M CH$_3$COOH, boiling for 30 min | 0.05 | 1.0 |
| 10% TCA, at RT | 0.01 | 0.2 |
| 90% Methanol vacuum-dried at RT | 0.2 | 4.0 |
| Acetone vacuum-dried at RT | 0.001 | 0.02 |
| Acetone precipitate resuspended in 0.10 M Hepes, pH 7.0 at RT | 5 | 100 |

EXAMPLE 8

Initial Characterization of hCG-RF Activity

Apparent GnRH immuno-activity, derived from the placenta following acetone precipitation and Tris-DTT-pepstatin buffer extraction, was only slightly precipitated during centrifugation at 4,000 to 100,000 − g. Following application of step-wise increases in centrifugal force of 4,000, 10,000, 40,000 and 100,000 × g, only 6.6%, 0.5%, 0.7% and 1.4% of the activity, respectively, was precipitated.

Diaflo filtration resulted in retention of 99% of the apparent GnRH immuno-activity using membranes as large as a PM-30, which indicates a mol wt of >30,000. Chromatography of the neutral placental extracts on Sephadex G-150 (90×5 cm column equilibrated in Tris-DTT-pepstatin) demonstrated that this chorionic apparent GnRH immunoactivity had a mol wt of 50,000–70,000, since it eluted as a single peak with a Ke =0.27–0.40 (See FIG. 1). Ninety-nine percent of the initial apparent GnRH immuno-activity was recovered following Sephadex chromatograpy. Using the same conditions, synthetic GnRH eluted with a Ke of 0.95.

Attempts to displace labeled GnRH by pre-incubation with this high mol wt placental hCG-RF were unsuccessful. When placental extracts and $^{125}$I-GnRH were incubated at 4° C. overnight and subjected to Sephadex G-150 column chromatography, <0.001% of the radioactivity eluted in the high-mol wt area with 99% in the GnRH area. This was similar to the elution of the control column, i.e. $^{125}$IGnRH incubated with diluent only. Incubatir,n of placental extract overnight did not alter its elution from that shown in FIG. 1.

Attempts to dissociate this high mol wt apparent GnRH immuno-activity to a smaller-mol-wt apparent GnRH immunoactivity using either guanidine (3 or 6M) or urea (1 or 2M) after 4 h of incubation at room temperature were unsuccessful. These treatments denatured and totally destroyed the apparent GnRH immuno-activity of these placental extracts. This loss of activity was immediate for guanidine and time-dependent for urea (Table 2). When synthetic GnRH was incubated for 4 h with guanidine or urea, there was no loss of immuno-activity. Incubation of placental extracts containing apparent GnRH immunoactivity with Triton X-100 for 3 h did not destroy the apparent GnRH immuno-activity, nor did it alter its chromatographic mobility, i.e. it eluted as a high-mol-wt protein. Buffer controls demonstrated the small volumes of urea, guanidine or Triton X-100 (10 ul) used in these assays did not interfere with its binding.

Inactivation of the apparent GnRH immuno-activity was also effected by boiling with 2M CH$_3$COOH for 30 min; only 1.0% of the initial apparent GnRH immuno-activity was recovered. Denaturation also occurred with exposure to 0.2M or 0.1M CH$_3$COOH. The small amount of apparent GnRH immuno-activity remaining (1%) after exposure to acid ((0.1, 0.2 or 2M) eluted on Sephadex G-25 chromatography as a population of small molecular weight molecules, not as a single peak. Similar studies using synthetic GnRH resulted in no loss of the apparent GnRH ixm:uno-activity and it still eluted on Sephadex G-25 column as a single sharp peak with a Ke of 0.60–0.80. Buffer controls did not interfere with assay binding.

TABLE 2

EFFECT OF UREA AND GUANIDINE (pH 7.5) ON APPARENT GnRH IMMUNO-ACTIVITY IN PLACENTAL EXTRACTS

| Time (min) | % of Original apparent GnRH immuno activity | | |
|---|---|---|---|
| | H$_2$O | Guanidine (3 M) | Urea (2 M) | Urea (1 M) |
| 0 | 100 | <6.5 | 72.7 | 100.0 |
| 10 | — | — | 59.4 | 91.0 |
| 20 | — | — | 29.2 | 91.0 |
| 30 | — | — | 12.4 | 79.2 |
| 60 | 100 | — | 4.8 | 51.1 |
| 90 | — | — | 4.6 | 35.3 |
| 120 | — | <6.5 | 2.5 | 30.8 |
| 240 | 100 | <6.5 | 1.6 | 30.9 |

EXAMPLE 9

Purification and Isolation of the High Molecular Weight Apparent GnRH Immuno-Activity in Placentas, i.e. Human Chroionic Gonadotropin Releasing Factor (hCG-RF)

Figure 1:
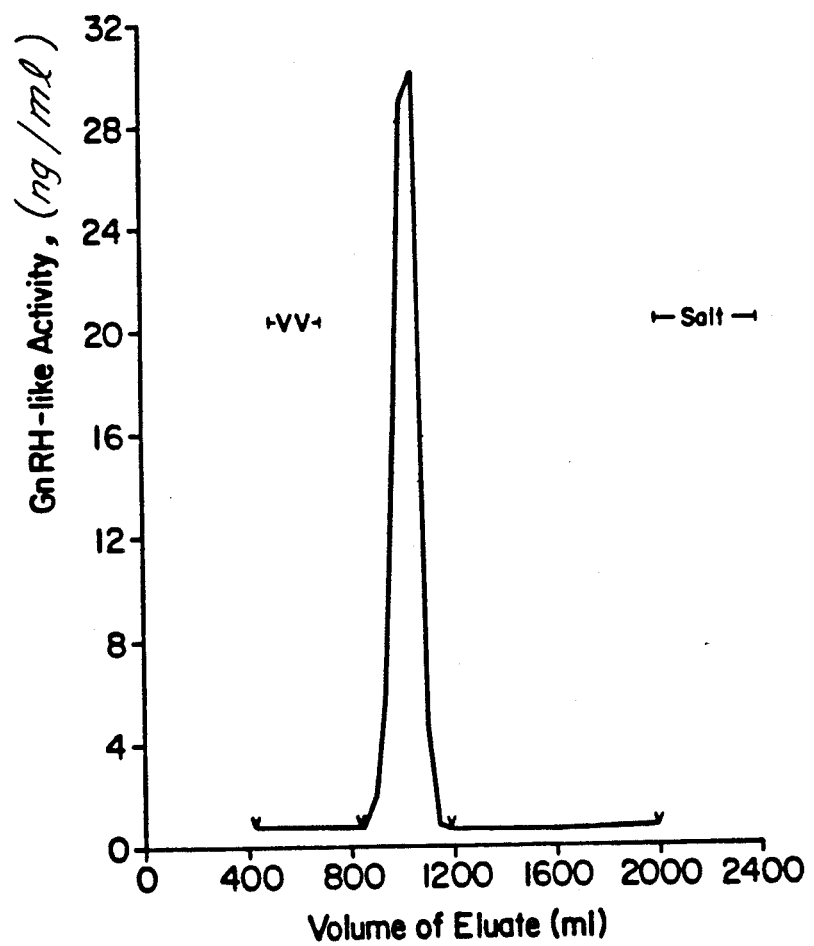
FIG. 1 describes the elution of placental hCG-RF from Sephadex G150 (5—90 cm in 0.01M Tris, 0.001 M dithiothreitol (DTT), 0.0004% pepstatin, pH 7.0) as determined from its apparent GnRH immuno-activity. Synthetic GnRH eluted in the salt area and bovine serum albumin (BSA) in the peak area (800-1200 ml).
Figure 2:
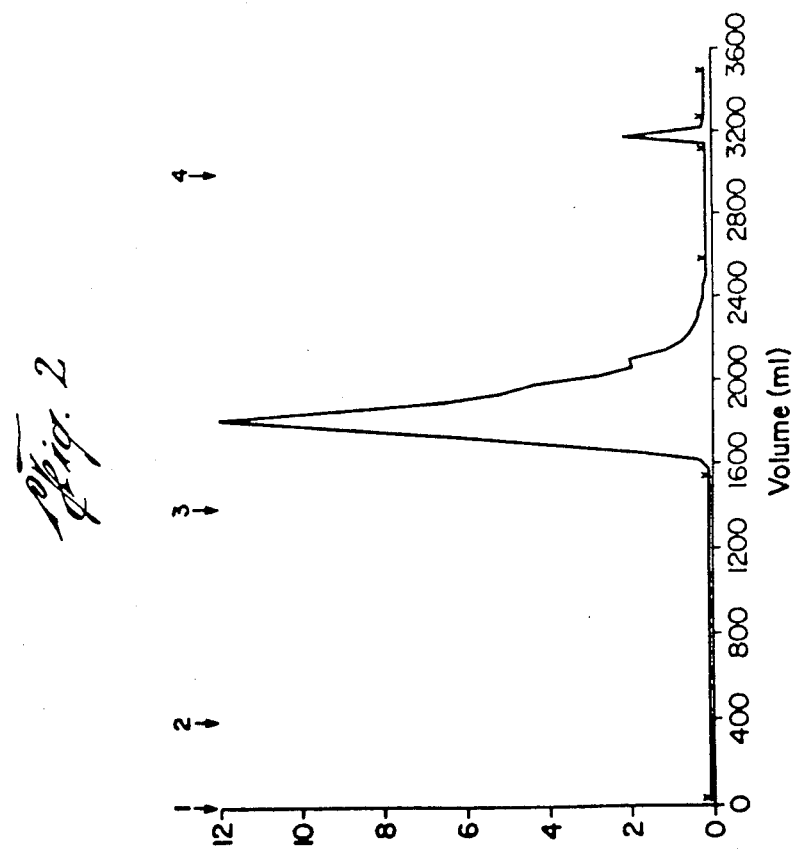
FIG. 2 describes the elution of hCG-RF, as determined from its apparent GnRH immuno-activity, from a DEAE-Sepharose column (2.6—70 cm, 0.01M Tris, 0.001M DTT, pH 7.4). The column was first washed with 400 ml column buffer (1), and then column buffer with 0.10M NaCl (2), apparent GnRH immuno-activity (hCG-RF) was eluted with 0.11M NaCl (3). Additional 1M NaCl (4) eluted another 2% of the apparent GnRH-like immuno-activitY..

Following acetone precipitation (600 ml x 2) of the placental apparent GnRH immuno-activity from a lyophilized, pulverized term placenta, the precipitate was extracted with Tris-DTT-pepstatin buffer (300 ml). Following centrifugation (3000×g for 30 min at 4° C), approximately 5 ug of apparent GnRH immuno-activity was obtained in the 160 ml supernatant. Chromatography of ecual volumes of the supernatant on two similar Sephadex G-150 columns (5 cm−90 cm equilibrated in Tris-DTTpepstatin buffer) resulted in 99% of the original apparent GnRH immuno-activity being eluted as a single peak with a Ke of 0.27–0.40 (FIG. 1). The fractions with apparent GnRH immuno-activity were pooled (300 ml per column, total 600 ml) and concentrated by Diaflo filtration. The retentate (60 ml) contained 99% of the apparent GnRH immuno-activity originally extracted. This partially purified concentrate of apparent GnRH immuno-activity was then applied to a DEAE-Sepharose column. The apparent GnRH immuno-activity was isolated by first washing this column with Tris-DTT and Tris-DTT buffer containing 0.10M NaCl, then eluting the apparent GnRH immuno-activity with Tris-DTT buffer containing 0.11M NaCl (FIG. 2). The apparent GnRH immuno-activity recovered was approximately 90% of that initially extracted, i.e. 4.5 ug of apparent GnRH immuno-activity. The final wash with 1M NaCl resulted in the elution of only another 1–2% of the original apparent GnRH immuno-activity. This purification was also monitored with both the monoclonal and polyclonal GnRH-RIAs and essentially identical findings were observed. Due to its unique physiochemical properties, as described herein, this molecule was termed human chorionic gonadotropin releasing factor (hCG-RF). The purified hCG-RF recovered was equivalent to about 28 mg of protein/term placenta. This calculation takes into account the greater mol wt as compared to the standard synthetic GnRH (60,000 versus 1200) and its limited activity in the GnRH assay (0.8%). Apparent reactivity in the GnRH assay was determined by comparing a known mass of highly purified hCG-RF as determined by optical density and Lowry protein measurements (using a BSA standard) to synthetic GnRH.

EXAMPLE 10

Physical and Chemical Characterization and Assessment Purity of hCG-RF

The highly purified hCG-RF fraction obtained following DEAE-Sepharose chromatography migrated as a single protein band ($R_f=0.22$) during PAGE, using 10% polyacrylamide gels and 0.1% SDS. When compared to standard proteins, a mol wt of 60,000 was estimated (FIG. 4). Using 7.5% gels with no SDS, a single band was also observed ($R_f=0.4$). Only a single band was visualized using the Schiff's Periodate stain on the SDS-PAGE gels of the highly purified hCG-RF (FIG. 3. This band had the same Rf as the single protein band visualized for purified hCG-RF, using the Coomassie brilliant blue staining. This glycoprotein, hCG-RF, had an apparent mol wt of about 60,000 (between 50,000 and 70,000) when compared to standards.

Using the molecular sizing HPLC system (Biorad TSK250), the same highly-purified hCG-RF eluted as a single protein peak (FIG. 4). All the apparent GnRH immuno-activity was associated with this single protein peak having an approximate 60,000 mol wt. Reapplication of this hCG-RF eluate to the HPLC system resulted in the same elution pattern as before. In this same system, synthetic GnRH eluted, as expected, as a small peptide at 22.0–25.5. min.

Trypsin digestion using 0.02 mg trypsin/ml of purified hCG-RF for 30 min at 37° C. had no effect on the apparent GnRH immuno-activity. However, incubation with 1 mg trypsin/ml for a similar time resulted in a 60% loss of apparent GnRH immuno-activity. Further incubation of hCGnRH in the 1 mg/ml trypsin solution for 1 h at 21° C. resulted in a further loss of apparent GnRH immunoactivity to 10% of its initial value. HPLC analyses of the 0.02 and 1.0 mg/ml trypsin-hCG-RF 30 min incubate revealed the only apparent GnRH immuno-activity eluted as a 60,000 mol wt substance, as had done the hCG-RF not treated with trypsin.

EXAMPLE 11 hCG-RF Biological activity

Figure 5:
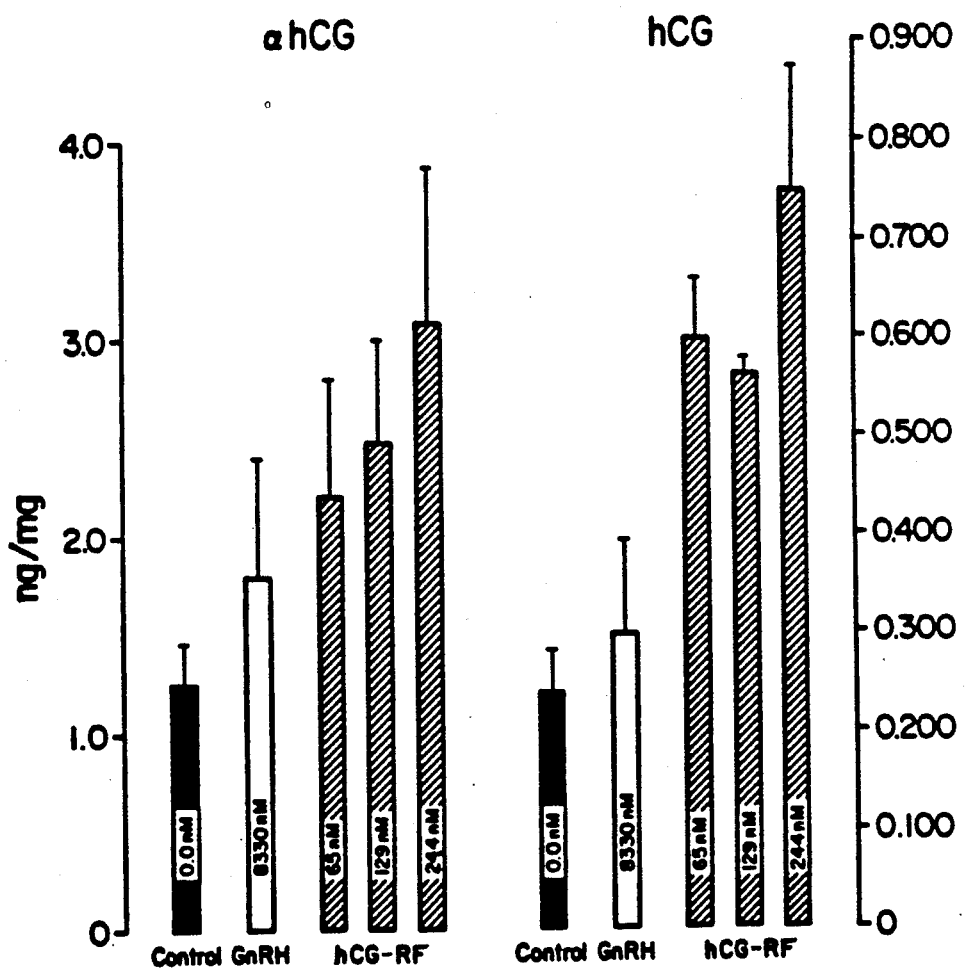
FIG. 5 describes the stimulation of alpha-hCG and hCG production (ng/mg placental tissue, mean±SEM) on day 7 of term placental cultures incubated with GnRH or hCG-RF as compared to controls.

The biological effect of hCG-RF on placental hormone release was assessed and compared to that of synthetic GnRH on a molar basis. Purified hCG-RF stimulated the release of alpha-hCG, hCG, prostaglandin E and 13,14-dihydro-15-keto prostaglandin F. A two- to threefold stimulation of alpha-hCG and hCG was effected by hCG-RF on days 5 and 6 of culture. The experiment was repeated using two different placentas. A dose-related stimulation of hCG and alpha-hCG ($p < 0.025$) was observed using 65–244 nM hCG-RF (FIG. 5). A stimulation of alpha-hCG and hCG was also observed using synthetic GnRH, but 8.33 uM was only as effective as 80 and 36 nM hCG-RF, respectively. Thus, on a molar ratio, hCG-RF was 100- and 230-fold more active in stimulating alpha-hCG and hCG release, respectively, than GnRH.

Figure 6:
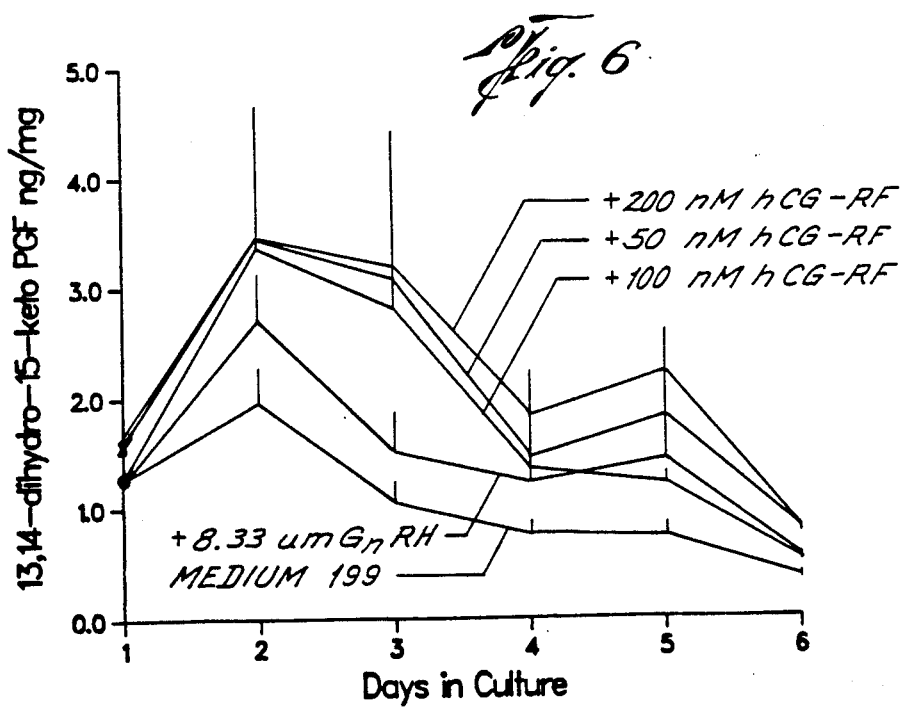
FIG. 6 describes the release of 13,14-dihydro-15-keto prostaglandin (ng/mg placental tissue, mean±SEM)

Prostaglandin release was also stimulated by hCG-RF and high doses of GnRH. On the second day of culture, the prostaglandin E and 13,14-dihydro-15-keto prostaglandin F were significantly increased (two- to threefold) using as little as 50 nM hCG-RF. This stimulation was observed throughout the duration of culture (FIG. 6). Synthetic GnRH (8.33 uM) was added to parallel placental cultures, and was only as potent as 14 nM hCG-RF in stimulating prostaglandin release. Thus, hCG-RF was 600-fold more potent than GnRH in stimulating prostaglandin release.

The biological effect of hCG-RF on rat pituitary LH release was assessed in intact adult male rats and, when compared to synthetic GnRH on a molar basis, was much less potent. A twofold stimulation of LH was observed 10–50 min following administration of 2 nM hCG-RF. However, this was only one-thousandth as potent as synthetic GnRH. Using the rat pituitary in vitro assay, a dose-related increase in LH release was observed. However, hCG-RF was only 1/500–1/1000 as potent a GnRH in stimulating pituitary LH release.

EXAMPLE 12

Relative Amino Acid Contact of Purified hCG-RF

A sample of hCG-RF purified as described in Example 10 was subjected to acid hydrolysis and chromatographic amino acid analysis Table 3 shows the relative amino acid content for purified hCG-RF for 16 amino acids (TRP and TYR not included). This analysis indicated, that the hCG-RF could be characterized as having a ratio of aspariginyl plus glutomyl residues over lysine plus arginese residues (ASN-ASP)+(GLN-GLU)/LYS+ARG (9.39+12.81/9.82+4.06) of about 1.6.

TABLE 3

AMINO ACID ANALYSIS OF PURIFIED hCG-RF

| Amino Acid | Amino Acid per 100 |
|---|---|
| CYS | 4.48 |
| ASN-ASP | 9.39 |
| THR | 5.87 |
| SER* | 4.70 |
| GLN-GLU* | 12.81 |
| PRO* | 4.48 |
| GLY* | 4.48 |
| ALA | 10.03 |
| VAL | 7.04 |
| MET | 1.60 |
| ILE | 2.56 |
| LEU* | 10.67 |
| PHE | 5.55 |
| HIS* | 2.99 |
| LYS | 9.82 |
| ARG* | 4.06 |

*Asterisks indicate amino acids present in the GnRH decapeptide (which contains 2 glycines one of each of the other marked amino acids and also TRP and TYR).

EXAMPLE 13

Use of a hCG-RF Preparation to Affect a State of Pregnancy

Purified hCG-RF was injected intra-amniotically (500 ug in 4 ml of 10 mM Hepes, 1 mM DTT, pH 7.4) into two pregnant baboons at 170 days of gestation. One baboon delivered a normal liveborn 3 hours following. The other pregnancy continued to term, delivering a normal liveborn on day 179.

EXAMPLE 14

Attempts to Produce a Hybridoma Secreting a Monoclonal Antibody Specific for hCG-RF Three mice (BLB/C) were immunized by intraperitoneal administration (ea. 100 mg each) of hCG-RF by a standard dosage schedule. Mouse spleen cells were hybridized with P3K myeloma cells to form hybrid cells. The hybrid cells were plated and grown in HAT selective medium. During the process of selective cloning, the antibody production declined concomitantly with loss of cell viability. These findings were reproducible. It appears that anti-hCG-RF production may inhibit continued growth and function of these hybridoma clones.

The above Examples report the purification and isolation of a glycoprotein from the human placenta which is a potent stimulant of hCG, alpha-hCG, and prostaglandin production. This hCG-RF accounts for 99% of the apparent GnRH immuno-activity in neutral extracts of the acetone precipitate of the human placenta.

The study of extraction procedures other than those typically used for GnRH, (e.g. acetone, ethanol, methanol, or acid); and use of neutral phosphate, Tris, or Hepes buffer extractants, made it possible to extract virtually all the apparent radio-immunoassayable GnRH immuno-activity from the placenta. The inability to precipitate the apparent GnRH immuno-activity at 10,000− g, where the GnRH receptor precipitates, or to bind labeled GnRH to this high mol wt substance, established that this large apparent GnRH immuno-activity was not due to receptor-bound GnRH. In addition, the finding that neither Triton X-100, guanidine nor urea could convert this large-mol-wt, apparent chorionic GnRH immuno-activity to a smaller-molwt GnRH indicated that its molecular size was not due to non-covalent binding of a smaller GnRH to a large protein. The detrimental effects of guanidine or urea on the apparent GnRH immuno-activity demonstrated that this molecule was dependent on its secondary and tertiary structure for retention of its apparent GnRH immuno-activity. The finding that the apparent GnRH immuno-activity of this molecule was labile to boiling and acid also distinguished it from synthetic GnRH. The generation, upon boiling or acid treatment, of some smaller molecules with reduced immuno-activity suggested that peptide bonds may have been cleaved by this treatment to produce less active fragments. The finding that the apparent GnRH immuno-active material in the placenta was precipitated with ethanol, methanol, or acetone indicated that this material was associated with, or was, protein in nature. These data also explain earlier descriptions of only the decapeptide in methanol, acid placental extracts. The susceptability of this high molecular weight apparent GnRH immuno-activity to trypsin digestion confirmed that it was proteinaceous. Also, the finding that more than 99% of this apparent immunoactivity was associated with a substance of >30,000 mol wt was consistent with it being a protein.

The possibility that this large chorionic apparently GnRH immuno-active material was actually a precursor of the decapeptide GnRH also seems unlikely. First, its activity exhibited different chemical lability, i.e. chorionic apparent GnRH immuno-activity was destroyed with guanidine, urea, or acid, while the decapeptide, GnRH, was not affected. Second, there was no conversion observed, during the purification process or after trypsin digestion, of this high-mol-wt apparent GnRH immuno-activity to a smaller-mol-wt GnRH. Third, the apparent immuno-activity of this high mol wt GnRH was dependent on its secondary or tertiary structure. This apparent GnRH immuno active material degrades GnRH. Last, biosassay studies indicated that the placental receptor was more responsive to the larger mol wt hCG-RF than to synthetic GnRH decapeptide.

This high molecular weight molecule, termed hCG-RF, appeared to represent a protein distinct from any protein coded by the nucleotide sequence which reported to contain within it a code for the GnRH decapeptide sequence. The total sequence reported by Seeburg et al (Nature (1984) V 311 p 666) was for 92 amino acids and, if processed, would yield a protein not greater than 11,000 mol wt--much smaller than the hCG-RF described herein. Possibly, the code described by Seeburg et al, when expressed, is the precursor of placental GnRH decapeptide or decapeptide precursor isolated by others. The presence of more than one size of apparent GnRH immuno-activity in the same tissue has been reported previously. Gautron et al. (Mol Cell. Endocrinol. (1981) V 24 p 1 ) described three mol wts for GnRH activity in the rat. Most of the hypothalamic GnRH was a low mol wt peptide, while that in the placenta was a high mol wt.

The purification of the apparent GnRH immuno-activity in placenta, hCG-RF, was most efficiently effected only after consideration of its lability and large molecular size. Sephadex chromatography of placental extracts indicated an approximate molecular weight of 50,000 to 70,000 for hCG-RF. This molecular size was confirmed by both HPLC and SDS-PAGE analysis of a highly purified hCGRF, which was obtained following ion exchange chromatography, resulting in a substantially purified preparation at least 99% pure (as determined by the HPLC and SDS-PAGE analysis). PAGE analysis using Schiff's periodate staining also demonstrated that this protein contained sugar moieties, that is, it was a glycoprotein.

Placental bioactivity studies demonstrated that purified hCG-RF was far more potent (100, 230 and 600-fold, respectively) in stimulation of placental alpha-hCG, hCG and prostaglandin production than was a similar molar concentration of synthetic GnRH. This finding suggested that the placental receptor had a much higher affinity for hCG-RF than for synthetic GnRH. Conversely hCG-RF appeared to have a much lower activity on the pituitary than did synthetic GnRH.

The above-presented data demonstrated that 99% of apparent GnRH immuno-activity of human term placenta was due to an about 60,000 mol wt sized glycoprotein, hCG-RF. Taken together with the finding that hCG-RF was a much more potent stimulant of placental hCG and prostaglandins production than was GnRH and was the most abundant apparent GnRH immunoactivity in the placenta, it may be concluded that hCG-RF, and not the decapeptide, GnRH, was the dominant form of hCG-stimulating activity in the placenta. This conclusion was further strengthened by the finding that the placental receptor had only a low affinity for synthetic GnRH.

The amino acid analysis of purified hCG-RF described in Example 12 and Table 3 indicated a broad typically proteinaceous array of amino acids.

As described in Example 13, a preparation comprising hCG-RF and a pharmaceutically acceptable carrier (in this specific case a non-toxic aqueous buffered solution) may be used to affect a state of pregnancy. In this preliminary showing, with one baboon a state of labor was induced which resulted in a live birth within 3 hours of the intraamniotic administration of 500 ug hCG-RF. It is contemplated that hCG-RF may be used to induce labor in humans, particularly since a human hormone was shown to be effective with the baboon. An intraamniotic dose of between about 100 ug and about 1000 ug hCG-RF is contemplated as effective for inducing mammalian labor. It appears that hCG-RF may be used as a mammalian abortifacient, although this need be supported by further experimentation. Although only an intraamniotic dosage of hCG-RF was tested, numerous other dosage routes known to those skilled in the art are contemplated as effective for induction of labor.

Antagonists or antibodies to hCG-RF may, at appropriate doses, be used to terminate pregnancy. We have shown antagonists to GnRH to effect this action and propose that antagonists or antibodies to the natural hormone, hCG-RF, will be even more effective. On the other hand, inhibition of hCG-RF action during premature labor or normal labor by an antagonist or antibody to it may be useful in inducing the cessation of labor.

The difficulties encountered in isolating a hybridoma which produced antibodies to hCG-RF have been reproduceable but not fully understood. Gupta et al. demonstrated the development of a hybridoma producing antibodies specific for GnRH (Am. J. Reprod. Immunol. Microbiol.

(1985) V 7 pp 104–108). It may be that free hCG-RF is essential to the function of murine hybridomas and possibly other cells without normal reproductive controls. It is contemplated that hCG-RF may be essential to certain neoplastic cell types and that antibodies to hCG-RF or hCG-RF antagonists may have anti-neoplastic effectiveness.

Changes may be made in the operation and arrangement of the various elements, steps and procedures described herein without departing from the concept and scope of the invention as defined in the following claims. For example hCG-RF may be synthesized or an analogous hormone from other species obtained and similarly used.

What is claimed is:

1. A 4,000 fold purified human chorionic gonadotropin releasing factor obtained from human placenta, with a molecular weight between about 50.000 daltons and about 70.000 daltons, said factor degrading GnRH.

2. A 4,000 fold purified human chorionic gonadotropin releasing factor preparation obtained from human placenta which is a glycoprotein with a molecular weight between about 50.000 daltons and about 70.000 daltons and is capable of stimulating release of human chorionic gonadotropin and prostaglandins from a human placental culture, said factor degrading GnRH.

3. A 4,000 fold purified human chorionic gonadotropin releasing factor preparation from human placenta which degrades GnRH and stimulates the release of human chorionic gonadotropin and prostaglandin from a human placental culture and has a molecular weight between about 50,000 daltons and about 70,000 daltons.

4. A 4,000 fold purified human chorionic gonadotropin releasing hormone preparation which degrades GnRH, comprising a glycoprotein isolated from human term placenta which has a molecular weight between about 50,000 daltons and about 70,000 daltons, and is capable of stimulating the release of human chorionic gonadotropin and prostaglandins from human placental explant cultures.

5. A process for preparing chorionic gonadotropin releasing factor comprising:
   defatting lyophilized pulverized term placenta with acetone
   extracting defatted material with an aqueous buffer having a pH of from about 7.0 to about 9.0 which preserves GnRH-degrading activity;
   obtaining from said extract a chorionic gonadotropin releasing factor having a molecular weight between about 50,000 and about 70,000 daltons, said factor being a glycoprotein which degrades GnRH and stimulates the release of prostaglandin and gonadotropin from human placental tissue.

6. A human chorionic gonadotropin releasing factor obtainable from human placenta and catalyzing the degradation of GnRH.

7. A hydrolytic enzyme obtainable from human placenta, having a molecular weight between about 50,000 daltons and about 70,000 daltons, and hydrolyzing peptide bonds of GnRH.

8. A method for the preparation of a 4,000- fold purified human placental hCG-RF protein from human placental tissue, comprising the steps of:
   (a) obtaining an amount of human placental tissue;

(b) dissecting membranes and vessels from the placental tissue to form processed human placental tissue;

(c) lyophilizing the processed placental tissue to form lyophilized human placental tissue;

(d) defatting the lyophilized human placental tissue with acetone and collecting an acetone precipitate;

(e) extracting hCG-RF from the placental acetone precipitate with an aqueous buffer having a pH of about 7.0 to about 9.0 form a placental suspension;

(f) collecting a placental supernatant from the placental suspension;

(g) collecting a placental eluate from the placental supernatant through a chromatography column;

(h) dialyzing and concentrating the human placental eluate to form a concentrated human placental eluate;

(i) applying the concentrated human placental eluate to a diethylaminoethyl ion exchange filtration dextran bead column;

(j) washing the column with a NaCl buffer to collect a purified humand placental eluate; and (k) concentrating the purified human placental eluate to form a 4,000-fold purified preparation of human placental hCG-RF protein.

9. The method of claim 8 wherien the aqueous buffer of step (e) is further defined as comprising tris(hydroxymethyl) amino methane-dithiothreitol buffer.

10. The method of claim 8 wherein the aqueous buffer of step (e) is 10 mM tris(hydroxymethyl) amino methane-1 mM dithiothreitol.

11. A purified preparation of human chorionic gonadotropin releasing factor obtained from human placenta, said factor being a glycoprotein having a molecular weight from about 50,000 to about 70,000 daltons; said factor stimulating the release of human chorionic gonadotropin and prostaglandin from human placental cultures; said factor comprising a GnRH-degrading enzymatic activity; and said factor hydrolyzing peptide bonds to render GnRH immunologically and biologically inactive.

12. A glycoprotein human chorionic gonadotropin releasing factor obtained from human placenta, said factor having a molecular weight between about 50,000 daltons and about 70,000 daltons, and being capable of catalyzing the degradation of GnRH and stimulating the release of prostaglandin and gonadotropin from human placental tissue.

* * * * *

UNITED STATES PATENT AND TRADEMARK OFFICE
CERTIFICATE OF CORRECTION

PATENT NO. : 4,945,055

DATED : July 31, 1990

INVENTOR(S) : Thomas J. Kuehl, M.J.K. Harper, Gabriel S. Khodr, Theresa M. Siler-Khodr It is certified that error appears in the above-identified patent and that said Letters Patent is hereby corrected as shown below:

In claim 1, column 18, line 21, delete "50.000" and insert --50,000--

In claim 1, column 18, line 22, delete "70.000" and insert --70,000--

In claim 2, column 18, line 26, delete "50.000" and insert --50,000--

In claim 2, column 18, line 26, delete "70.000" and insert --70,000--

In claim 4, column 18, line 42, insert the word --term-- between the words 'human' and 'placental'

In claim 5, column 18, line 51, insert the word --and-- after the word 'activity'

In claim 8(e), column 19, line 12, insert the word --to-- between '9.0' and 'form'

UNITED STATES PATENT AND TRADEMARK OFFICE
CERTIFICATE OF CORRECTION

PATENT NO. : 4,945,055
DATED : July 31, 1990
INVENTOR(S) : Thomas J. Kuehl, M.J.K. Harper, Gabriel S. Khodr, Theresa M. Siler-Khodr It is certified that error appears in the above-identified patent and that said Letters Patent is hereby corrected as shown below:

In claim 8(j), column 19, line 27, delete "humand" and insert --human--

Signed and Sealed this

Seventh Day of January, 1992

Attest:

HARRY F. MANBECK, JR.

Attesting Officer

Commissioner of Patents and Trademarks